(12) United States Patent
Köstler et al.

(10) Patent No.: US 9,708,538 B2
(45) Date of Patent: *Jul. 18, 2017

(54) FLAME PROTECTION AGENT COMPOSITIONS CONTAINING TRIAZINE INTERCALATED METAL PHOSPHATES

(75) Inventors: Hans-Günter Köstler, Heppenheim (DE); Trupte Dave, Zwingenberg (DE); Wolfgang Wehner, Zwingenberg (DE)

(73) Assignee: J.M. Huber Corporation, Atlanta, GA (US)

( * ) Notice: Subject to any disclaimer, the term of this patent is extended or adjusted under 35 U.S.C. 154(b) by 798 days.

This patent is subject to a terminal disclaimer.

(21) Appl. No.: 13/818,672

(22) PCT Filed: Aug. 5, 2011

(86) PCT No.: PCT/EP2011/063567
§ 371 (c)(1),
(2), (4) Date: May 8, 2013

(87) PCT Pub. No.: WO2012/025362
PCT Pub. Date: Mar. 1, 2012

(65) Prior Publication Data
US 2014/0361230 A1    Dec. 11, 2014

(30) Foreign Application Priority Data
Aug. 23, 2010   (DE) .......................... 10 2010 035 103

(51) Int. Cl.
*C09K 21/12*  (2006.01)
*C07D 487/16* (2006.01)
(Continued)

(52) U.S. Cl.
CPC ............ *C09K 21/12* (2013.01); *C07D 251/54* (2013.01); *C07D 251/70* (2013.01);
(Continued)

(58) Field of Classification Search
None
See application file for complete search history.

(56) References Cited

U.S. PATENT DOCUMENTS 4,373,103 A * 2/1983 Jung .................... C07D 251/54
544/195
4,714,724 A * 12/1987 Jung .................... C07D 251/54
524/100
(Continued)

FOREIGN PATENT DOCUMENTS

DE       4001805      7/1991
DE    102007036465    2/2009
(Continued)

OTHER PUBLICATIONS

Nakayama, "Intercalation of Organic Molecules into Layered Phosphates", Phosphorus Research Bulletin, Bd. 23, 2009, Seiten 1-9, XP55017083, ISSN: 0918-4783, DOI: 10.3363/prb.23.1.
(Continued)

*Primary Examiner* — Joseph D Anthony
(74) *Attorney, Agent, or Firm* — Eversheds Sutherland (US) LLP

(57) ABSTRACT

The present invention relates to flame retardant compositions comprising (a) at least one triazine-intercalated metal phosphate with open framework structure with at least one monomer unit of the following general formula (I):

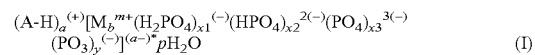

and (b) at least one flame retardant component other than (a). The invention further relates to the use thereof, the specific compounds of the general formula (I) and to the preparation thereof.

22 Claims, 3 Drawing Sheets

(51) Int. Cl.
*C07D 251/70* (2006.01)
*C07D 251/54* (2006.01)
*C07F 9/6571* (2006.01)
*C08K 5/00* (2006.01)
*C08K 5/52* (2006.01)
*C08K 5/5313* (2006.01)
*C08G 79/04* (2006.01)

(52) U.S. Cl.
CPC ...... *C07D 487/16* (2013.01); *C07F 9/657172* (2013.01); *C08G 79/04* (2013.01); *C08K 5/0091* (2013.01); *C08K 5/5205* (2013.01); *C08K 5/5313* (2013.01)

(56) References Cited

U.S. PATENT DOCUMENTS

| | | | |
|---|---|---|---|
| 5,182,049 | A | 1/1993 | von Bonin |
| 6,653,474 | B1 | 11/2003 | Kersjes et al. |
| 6,737,456 | B2 | 5/2004 | Bar-Yakov et al. |
| 7,851,532 | B2 | 12/2010 | Kim et al. |
| 8,754,154 | B2* | 6/2014 | Dave .................. C07F 9/3808 524/100 |
| 9,200,122 | B2* | 12/2015 | Dave .................. C08K 5/5317 |
| 2004/0082697 | A1 | 4/2004 | Ratzsch et al. |
| 2009/0105387 | A1* | 4/2009 | Wehner ............... C08K 5/005 524/425 |
| 2011/0105654 | A1 | 5/2011 | Dicke et al. |
| 2011/0178212 | A1 | 7/2011 | Dicke et al. |
| 2011/0245383 | A1 | 10/2011 | Dave et al. |
| 2014/0361230 | A1* | 12/2014 | Kostler .............. C07D 251/54 252/607 |
| 2014/0364570 | A1* | 12/2014 | Dave .................. C08K 5/5317 525/186 |
| 2015/0252065 | A1* | 9/2015 | Wehner .............. C07F 3/003 524/100 |
| 2015/0376375 | A1* | 12/2015 | Leistner ............. C08K 5/098 524/100 |
| 2016/0053088 | A1* | 2/2016 | Dave .................. C08K 5/5317 524/100 |

FOREIGN PATENT DOCUMENTS

| | | |
|---|---|---|
| DE | 2008016964 | 10/2009 |
| DE | 102008016967 | 10/2009 |
| JP | H09-104804 | 4/1997 |
| WO | 0248248 | 6/2002 |
| WO | 2009015772 | 2/2009 |

OTHER PUBLICATIONS

Alongi, et al., "Flame retardancy properties of [alpha]-zirconium phosphate based composites", Polymer Degradation and Stability, Bd. 95, Nr. 9, 27, 2010, Seiten 1928-1933, XP55017029, ISSN: 0141-3910, DOI: 10.1016/j.polymdegradstab.2010.04.2007.

XP002667710, "Melamine derivatives", SpecialChem S.A., 2009, Gefunden im Internet: URL:http://web.archive.org/web/200906289141703/http://www.specialchem4polymers.com/tc/Melamine-Flame-Retardants/index.aspx?id=4004 [gefunden am Jan. 20, 2012].

Hayashi, et al., "Intercalation of melamine into layered zirconium phosphates and their adsorption properties of formaldehyde in gas and solution phase", Solid State Sciences, 2009, 11(5): 1007-1015.

* cited by examiner

FLAME PROTECTION AGENT COMPOSITIONS CONTAINING TRIAZINE INTERCALATED METAL PHOSPHATES

CROSS REFERENCE TO RELATED APPLICATIONS

The present application is a National Stage Application claiming the priority of co-pending PCT Application No. PCT/EP2011/063567 filed Aug. 5, 2011, which in turn, claims priority from German Patent Application No. 10 2010 035 103.2 filed Aug. 23, 2010. Applicants claim the benefits of 35 U.S.C. §120 as to the PCT application and priority under 35 U.S.C. §119 as to the said German Patent application, and the entire disclosures of both applications are incorporated herein by reference in their entireties.

The present invention relates to flame retardant compositions comprising triazine-intercalated metal phosphates with open framework structures, to the use thereof, to such metal phosphates and to the preparation thereof.

It is known that organophilic sheet silicates which have been produced, for example, by means of ion exchange can be used as filler materials for thermoplastic materials and thermosets to obtain nanocomposites. In the case of use of suitable organophilic sheet silicates as filler materials, the physical and mechanical properties of the moldings produced in such a way are considerably improved. Of particular interest is the increase in the stiffness with at least equal toughness. Particularly good properties are exhibited by nanocomposites which comprise the sheet silicate in exfoliated form. These nanocomposites are preferably used as flame retardants or as synergists.

WO-A 00/44669 discloses organophilic sheet silicates which are prepared by treatment of a natural or synthetic sheet silicate or of a mixture of such silicates with a salt of an optionally quaternary cyclic melamine compound or a mixture of such salts.

Similar considerations should also apply to organophilic metal phosphates with open framework structures (see definition in "A Review of Open Framework Structures", *Annu. Rev. Mater. Sci.* 1996, 26, 135-151), especially to those intercalated with melamine (intercalates also called inclusion compounds; see definition in RÖMPP, Chemielexikon, 9th ed., 1995, G. Thieme, Vol. 3, p. 2005).

The literature describes various melamine phosphates which do not have open framework structures, for instance melamine orthophosphate in *Magn. Reson. Chem.* 2007, 45, p. 231-246, bismelamine di(pyro)phosphate in *J. Phys. Chem.* B 2004, 108, 15069-15076 and melamine polyphosphate in *J. Phys. Chem.* B 2005, 109, 13529-13537. The use thereof as flame retardants is mentioned therein in the secondary literature cited.

Certain melamine metal phosphates are described in WO-A 2009/015772. However, these compounds possess, as shown by the aluminum compound, only limited intrinsic (thermal) stability which is insufficient for incorporation into polyamides (see examples 7 and 8).

Melamine-intercalated (layered) zirconium phosphates are known from *Solid State Sciences* 2009, 11, 1007-1015. However, use as polymer additives, especially as flame retardants, is not described therein. Other melamine-intercalated layered (metal) phosphates are not documented in the literature.

Intercalation of α,ω-alkanediamines into (layered) aluminum triphosphate is published in *J. Inclusion Phenomena and Macrocyclic Chem.* 1999, 34 401-412.

The layer structure of aluminum triphosphate is documented in Chem. Commun. 2006, 747-749. An open network structure is known for ethylenediamine-zinc phosphate adducts from *Zeolites and Related Microporous Materials* 1994, 2229-2236.

Ethylenediaminebis(zinc phosphate) is claimed in U.S. Pat. No. 5,994,435 and U.S. Pat. No. 6,207,735 as a flame retardant. JP 8269230 describes amine-zinc phosphates which also include the anions $HPO_4$, $H_2PO_4$, $Zn_2(HPO_4)_3$ and $Zn_4[(PO_4)_2 (HPO_4)_2]$. Applications JP9040686, JP10259275, JP11152373, JP11199708, JP11246754, JP11269187, JP11293155, JP2000063562, JP2000063563, JP2000154283, JP2000154287, JP2000154324 and JP2001031408 describe processes for preparing specific embodiments and combinations of ethylenediamine-zinc phosphate. However, the processes are uneconomic since they either work with an $H_3PO_4$ excess or proceed from $Zn(en)_3$ complexes. JP9169784 and JP2001011462 publish diethylenetriamine or piperazine-zinc phosphate complexes as flame retardants.

Inorganic phosphates with open framework structures are described in an article in *Angew. Chem.* 1999, 111, 3466-3492.

Disadvantages of the prior art compounds mentioned are the limited intrinsic (thermal) stability and the unfavorable mechanical properties which result after incorporation into the polymer substrate.

It is an object of the present invention to provide flame retardant compositions which have a high degree of intrinsic (thermal) stability and impart outstanding mechanical properties to the polymer after incorporation.

The object was achieved, inter alia, by the provision of flame retardant compositions comprising (a) at least one triazine-intercalated metal phosphate with at least one monomer unit of the following general formula (I):

where

$(A\text{-}H)^{(+)}$ is a triazine derivative of the formula (II-1), (II-2) or (II-3)

melamine melam melem (II-3)

each M is independently Cu, Mg, Ca, Zn, Mn, Fe, Co, Ni, TiO, ZrO, VO, B, Si, Al, Sb, La, Ti, Zr, Ce or Sn;
a is 1 to 6,
b is 1 to 14,
m=1 to 4,
$x_1$, $x_2$, $x_3$, y=0 to 12, where at least one of the variables $x_1$, $x_2$, $x_3$>0 and p=0 to 5,
where: a+mb=$x_1$+2$x_2$+3$x_3$+y
and
(b) at least one further flame retardant component other than (a).

In a preferred embodiment of the invention, the flame retardant compositions comprising the triazine-intercalated metal phosphates (a) of the formula (I) have open framework structures. The triazine derivatives, and likewise melon, are known as chemical precursors for carbon nitride $(C_3N_4)_x$.

Triazine-intercalated metal phosphates, especially with open framework structures which are preferably prepared by direct reaction of (aqueous) acidic metal phosphates with melamine and subsequent pretreatment from the corresponding precursors, exhibit high thermal stability in processing combined with excellent dispersing action and interfacial adhesion. These systems feature surprisingly good layer separation, combined with excellent adhesion to a multitude of polymers and fillers. It is additionally surprising that the inventive triazine-intercalated metal phosphates with open framework structures are not only outstanding fillers for improving the mechanical properties of polymers, but also act as flame retardants. The triazine-intercalated (metal) phosphates with open framework structures may also consist of chain (ribbon) phosphates (catena type), sheet phosphates (ladder or phyllo type—all with 1-D structures), layered phosphates (with 2-D structures) or 3-D phosphates (zeolite type).

In a particularly preferred embodiment of the present invention, in the flame retardant compositions comprising component (a), (A-H)$^{(+)}$=(II-1) and M=Zn or Al.

Preferably, component (b) is at least one metal compound, which is not a metal phosphate of component (a), or/and at least one metal-free phosphorus compound.

This at least one metal compound (b) is preferably a metal oxide, a metal hydroxide, a metal phosphate, a metal pyrophosphate, a hydrotalcite, a cationically or anionically modified organoclay, a stannate or molybdate salt, a metal borate or metal phosphinate of the formula (III):

(III)

where $R^1$ and $R^2$ are each hydrogen or a straight-chain or branched $C_1$-$C_6$-alkyl radical or a phenyl radical; and Mt=Ca, Mg, Zn or Al and m=2 or 3, or a hypophosphite salt of the formula $M^{m+}[H_2PO_2]_m^{m-}$ (M=Al, Ca, Mg and Zn, and m=2 or 3).

Organoclays are understood to mean organophilically modified clay minerals (principally montmorillonite) based on cation exchange, such as triethanol-tallow-ammonium montmorillonite and triethanol-tallow-ammonium hectorite (Dr. G. Beyer; *Konf. Fire Resistance in Plastics* 2007). Anionic organoclays are organophilically modified hydrotalcites based on anion exchange with alkali metal rosinates, unsaturated and saturated fatty acid salts, and sulfonates and sulfates substituted by long-chain alkyl.

Particularly preferred metal oxides are diantimony trioxide, diantimony tetroxide, diantimony pentoxide or zinc oxide.

Particularly preferred metal hydroxides are aluminum hydroxide (ATH) or gibbsite (hydrargillite), aluminum oxo hydroxide (boehmite) and magnesium hydroxide (MDH, brucite), and hydromagnesite. In addition to gibbsite and boehmite, the other polymorphs of aluminum hydroxides should also be mentioned, namely bayerite, nordstrandite and diaspore.

Preferred metal phosphates are metal pyrophosphates. Particular preference is given to aluminum pyrophosphate and zinc pyrophosphate, and to zinc triphosphate and aluminum triphosphate, and likewise to aluminum metaphosphate and aluminum orthophosphate.

Preferred hydrotalcites are magnesium aluminum hydroxocarbonate and calcium aluminum hydroxocarbonate.

Among the cationically or anionically modified organoclays, particular preference is given to the alkyl sulfate- or fatty acid carboxylate-modified hydrotalcites or long-chain quaternary ammonium-modified clay minerals.

Among the stannate and molybdate salts, particular preference is given to zinc stannate, zinc hydroxy stannate, ammonium heptamolybdate and ammonium octamolybdate. Mention should likewise be made of other molybdates (including polymolybdates) such as calcium zinc molybdate, basic zinc molybdate and calcium molybdate.

Preferred borates are alkali metal and alkaline earth metal borates, and zinc borate. Mention should also be made of aluminum borate, barium borate, calcium borate, magnesium borate, manganese borate, melamine borate, potassium borate and zinc borophosphate.

Among the metal phosphinates, preference is given to calcium phosphinate, magnesium phosphinate, zinc phosphinate or aluminum phosphinate. Particular preference is given to calcium phenyl(benzene)phosphinate, magnesium phenyl(benzene)phosphinate, zinc phenyl(benzene)phosphinate or aluminum phenyl(benzene)phosphinate, and calcium diethyl(ethane)phosphinate, magnesium diethyl(ethane)phosphinate, zinc diethyl(ethane)phosphinate or aluminum diethyl(ethane)phosphinate.

Among the hypophosphites, particular preference is given to the magnesium, calcium, zinc and aluminum salts.

A further preference of the invention relates to flame retardant compositions comprising, as component (b), at least one metal-free phosphorus compound.

This at least one metal-free phosphorus compound (b) is red phosphorus, an oligomeric phosphate ester, an oligomeric phosphonate ester, a cyclic phosphonate ester, a thiopyrophosphoric ester, melamine pyrophosphate, melamine polyphosphate, ammonium polyphosphate, melaminium phenylphosphonate and the monoester salt thereof (WO2010/063623), melamine benzenephosphinate (WO2010/057851), hydroxyalkylphosphine oxides (WO2009/034023), tetrakis(hydroxymethyl)phosphonium salts and phospholane or phosphole derivatives, and bisphosphoramidates with piperazine as a bridging member or a phosphonite ester.

Oligomeric phosphate esters are of the formula (IV) or formula (V):

(IV)

(V)

where each R is independently hydrogen, $C_1$-$C_4$ alkyl or hydroxyl, n=1 to 3 and o is 1 to 10.

Particular preference is given to the oligomer where $R_n$=H and resorcinol or hydroquinone as a constituent of the bridging member, and $R_n$=H and bisphenol A or bisphenol F as a constituent of the bridging member.

Oligomeric phosphonate esters are preferably characterized by formula (VI):

(VI)

where $R^3$=methyl or phenyl and x is 1 to 20, and R, n are each as defined above.

Particular preference is given to the oligomer where $R_n$=H and resorcinol or hydroquinone as a constituent of the bridging member.

Cyclic phosphonate esters preferably have the following formula (VII):

(VII)

where y=0 or 2. Particular preference is given to bis[5-ethyl-2-methyl-1,3,2-dioxaphosphorinan-5-yl)methyl]methyl phosphonate P,P'-dioxide.

Thiopyrophosphoric esters are preferably characterized by the following formula (VIII):

(VIII)

Particular preference is given to 2,2'-oxybis[5,5-dimethyl-1,3,2-dioxaphosphorinane]2,2'-disulfide.

Among the hydroxyalkylphosphine oxides, preference is given to isobutylbis(hydroxymethyl)phosphine oxide and to the combination thereof with epoxy resins (WO-A 2009/034023).

Among the tetrakis(hydroxyalkyl)phosphonium salts, particular preference is given to the tetrakis(hydroxymethyl)phosphonium salts.

Among the phospholane or phosphole derivatives, particular preference is given to dihydrophosphole (oxide) derivatives and phospholane (oxide) derivatives, and to the salts thereof (EP 089 296 and EP 1024 166).

Particularly preferred among the bisphosphoramidates are the bis(diorthoxylyl) esters with piperazine as a bridging member.

Among the phosphonite esters, preference is given to phenyl benzenephosphinate and the PH-functionalized derivatives and DOPO derivatives thereof.

DOPO derivatives (9,10-dihydro-9-oxa-10-phosphaphenanthrene 10-oxide derivatives or 6H-dibenzo(c,e)(1,2-oxaphosphorin 6-oxide derivatives (preference being given to PH-functionalized derivatives)) include the compounds whose structures are as follows (cf. WO-A 2008/119693):

-continued

Particular preference is given to:

DOPO may also be replaced by dihydrooxaphosphaan-thracen(one) oxide. An overview thereof can be found in WO-A 2008/119693.

Further additives (synergists) include: polyols, aminouracils, tris(hydroxyethyl) isocyanurate (THEIC), melamine (iso)cyanurate, POSS compounds and expandable graphite.

Among the polyols, particular preference is given to pentaerythritol, dipentaerythritol and trip entaerythritol.

Among the aminouracils, particular preference is given to 1-methyl-6-aminouracil and 1,3-dimethyl-6-aminouracil.

POSS compounds (Polyhedral oligomeric Silsesquioxanes) and derivatives are described in detail in POLYMER, Vol. 46, pp 7855-7866. Preference is given here to POSS derivatives based on methylsiloxane.

In addition, it is also possible for tris(hydroxyethyl) isocyanurate polyterephthalates to be present, and also triazine polymers with piperazine-1,4-diyl bridging members and morpholin-1-yl end groups.

In addition, the following additives may be present: bisazinpentaerythrityl diphosphate salts, hexaaryloxytriphosphazenes, polyaryloxyphosphazenes and siloxanes $(R_2SiO)_r$ or $(RSiO_{1.5})_r$.

Metal oxides such as titanium dioxide, silicon dioxide; clay minerals such as kaolinite, muscovite, pyrophyllite, bentonite and talc, and other minerals such as wollastonite, quartz, mica, feldspar.

It is also additionally possible for dolomite, bentonite, huntite, or silicas and the natural or synthetic silicate minerals thereof, to be present in the polymer.

Moreover, in addition to the at least one inventive metal phosphate, foam formers may be added to a polymer. Foam formers include: melamine, melamine-formaldehyde resins, urea derivatives such as urea, thiourea, guanamines, benzoguanamine, acetoguanamine and succinylguanamine, dicyandiamide, guanidine and guanidine sulfamate, and other guanidine salts or allantoins and glycolurils.

Furthermore, a polymer comprising the at least one inventive metal phosphate may also comprise antidripping agents, especially based on polytetrafluoroethylene. The concentration of such antidripping agents is 0.01 to 15% by weight based on the polymer to be processed.

In addition, it is also possible to add further components to polymers comprising the at least one inventive metal phosphate, examples being fillers and reinforcers such as glass fibers, glass beads or mineral additives such as chalk. Further additives may be antioxidants, light stabilizers, lubricants, pigments, nucleating agents and antistats.

The present invention also relates to the use of the inventive triazine-intercalated metal phosphates with open framework structures as flame retardants in a polymer, paper, textiles or wood plastic composites (WPCs).

The inventive flame retardants are very suitable for imparting flame retardancy properties to synthetic, especially thermoplastic, polymers.

A particular embodiment of the invention relates to the use of the at least one inventive metal phosphate in a polymer as a flame retardant, said polymer being a thermoplastic which is preferably selected from the group consisting of polyamide, polycarbonate, polyolefin, polystyrene, polyester, polyvinyl chloride, polyvinyl alcohol, ABS and polyurethane, or being a thermoset which is preferably selected from the group consisting of epoxy resin (with hardener), phenol resin and melamine resin.

If the polymer in which the at least one inventive metal phosphate is used as a flame retardant is a thermoplastic, preference is given to polyamide, polyurethane, polystyrene, polyolefin or polyester.

If the polymer in which the at least one inventive metal phosphate is used as a flame retardant is a thermoset, preference is given to epoxy resin.

It is also possible to use mixtures of one or more polymers, especially thermoplastics and/or thermosets, in which the inventive metal phosphate is used as a flame retardant. Examples of such polymers are:

1) Polymers of mono- and diolefins, for example polypropylene, polyisobutylene, polybutene-1, poly-4-methyl-pentene-1, polyvinylcyclohexane, polyisoprene or polybutadiene, and polymers of cycloolefins, for example of cyclopentene or norbornene and polyethylene (including crosslinked), for example High Density Polyethylene (HDPE) or High Molecular Weight (HDPE-HMW), High Density Polyethylene with Ultra-High Molecular Weight (HDPE-UHMW), Medium Density Polyethylene (MDPE), Low Density Polyethylene (LDPE) and Linear Low Density Polyethylene (LLDPE), (VLDPE) and (ULDPE), and copolymers of ethylene and vinyl acetate.
2) Polystyrenes, poly(p-methylstyrene), poly($\alpha$-methylstyrene).
3) Copolymers and graft copolymers of polybutadiene-styrene or polybutadiene and (meth)acrylonitrile, for example ABS and MBS.
4) Halogenated polymers, for example polychloroprene, polyvinyl chloride (PVC), polyvinylidene chloride (PVDC), copolymers of vinyl chloride/vinylidene chloride, vinyl chloride/vinyl acetate or vinyl chloride/vinyl acetate.
5) Poly(meth)acrylates, polymethyl methacrylates (PMMA), polyacrylamide and polyacrylonitrile (PAN).
6) Polymers of unsaturated alcohols and amines or acyl derivatives or acetals thereof, for example polyvinyl alcohol (PVA), polyvinyl acetates, stearates, benzoates or maleates, polyvinyl butyral, polyallyl phthalates and polyallylmelamines.
7) Homo- and copolymers of cyclic ethers, such as polyalkylene glycols, polyethylene oxides, polypropylene oxides and copolymers thereof with bisglycidyl ethers.
8) Polyacetals such as polyoxymethylenes (POM), and polyurethane- and acrylate-modified polyacetals.
9) Polyphenylene oxides and sulfides, and mixtures thereof with styrene polymers or polyamides.
10) Polyamides and copolymers derived from diamines and dicarboxylic acids and/or from aminocarboxylic acids or the corresponding lactams, for example nylon 4, nylon 6, nylon 6/6, 6/10, 6/9, 6/12, 12/12, nylon 11, nylon 12, aromatic polyamides derived from m-xylylenediamine and adipic acid, and copolyamides modified with EPDM or ABS. Examples of polyamides and copolyamides are derived from 8-caprolactam, adipic acid, sebacic acid, dodecanoic acid, isophthalic acid, terephthalic acid, hexamethylenediamine, tetramethylenediamine, 2-methylpentamethylenediamine, 2,2,4-trimethylhexamethylenediamine, 2,4,4-trimethylhexamethylenediamine, m-xylylenediamine or bis(3-methyl-4-aminocyclohexyl)methane.
11) Polyureas, polyimides, polyamideimides, polyetherimides, polyesterimides, polyhydantoins and polybenzimidazoles.
12) Polyesters derived from dicarboxylic acids and dialcohols and/or hydroxycarboxylic acids or the corresponding lactones, for example polyethylene terephthalate, polypropylene terephthalate, polybutylene terephthalate, poly-1,4-dimethylcyclohexane terephthalate, polyalkylene naphthalate (PAN) and polyhydroxybenzoates, polylactic esters and polyglycolic esters.
13) Polycarbonates and polyester carbonates.
14) Polyketones.
15) Mixtures or alloys of the abovementioned polymers, e.g. PP/EPDM, PA/EPDM or ABS, PVC/EVA, PVC/ABS, PBC/MBS, PC/ABS, PBTP/ABS, PC/AS, PC/PBT, PVC/CPE, PVC/acrylate, POM/thermoplastic PU, PC/thermoplastic PU, POM/acrylate, POM/MBS, PPO/HIPS, PPO/N6,6 and copolymers, PA/HDPE, PA/PP, PA/PPO, PBT/PC/ABS or PBT/PET/PC, and also TPE-O, TPE-S and TPE-E.
16) Thermosets such as PF, MF or UF or mixtures thereof
17) Epoxy resins—thermoplastics and thermosets
18) Phenol resins.
19) Wood-plastic composites (WPC) and polymers based on PLA, PHB and starch.

The concentration of the at least one triazine-intercalated metal phosphate (a) claimed and component (b) in a polymer or a polymer mixture is preferably 0.1 to 60% by weight based on the polymer to be processed.

The material thus rendered flame-retardant by addition of the at least one inventive metal phosphate can be processed to give fibers, films, cast articles, and for treatment of surfaces.

The at least one inventive metal phosphate can also be used for surface treatment (impregnation) of fibers, films, textiles or other industrial materials.

The present invention further relates to the use of the inventive triazine-intercalated metal phosphates with open framework structures for the production of paints, adhesives, casting resins, coatings, thixotropic agents and flame retardants for polymers.

Accordingly, a further aspect of the present invention is the use of a composition of the present invention as a flame retardant in a polymer, paper, textile or wood plastic composite (WPC). In particular the polymer is a thermoplastic, preferably selected from the group consisting of polyamide, polycarbonate, polyolefin, polystyrene, polyester, polyvinyl chloride, polyvinyl alcohol, ABS and polyurethane, or is a thermoset, preferably selected from the group consisting of epoxy resin, phenol resin and melamine resin.

The present invention further relates to the use of the at least one inventive metal phosphate as a filler in polymers.

A further aspect of the present invention are compounds of the general formula (I)

(I)

where

(A-H)$^{(+)}$ is a triazine derivative of the formula (II-1, II-2 or II-3)

melamine melam (II-2)

melem (II-3)

each M=Al,
a is 2,
b is 1,
m is 3,
$x_1=0$ or 1, $x_2=0$ or 2, $x_3=1$ or 0, $y=2$ or 0 and p is 0 to 5 and wherein $a+mb=x_1+2x_2+3x_3+y$.

The present invention further provides a process for preparing the inventive metal phosphate, wherein a substance (A) is reacted with an acidic metal phosphate of the formula $H_a^{(+)}[M_b^{m+}(H_2PO_4)_{x1}^{(-)}(HPO_4)_{x2}^{2(-)}(PO_4)_{x3}^{3(-)}(PO_3)_y^{(+)}]^{(a-)}*pH_2O$.

In particular the present invention relates to a process for preparing the above mentioned compounds comprising the step of reacting a compound (A), where (A) is a triazine of the formula (II-4), (II-5) or (II-6)

melamine (II-4)

melam (II-5)

melem (II-6)

with an acidic metal phosphate of the formula $H_a^{(+)}[M_b^{m+}(H_2PO_4)_{x1}^{(-)}(HPO_4)_{x2}^{2(-)}(PO_4)_{x3}^{3(-)}(PO_3)_y^{((-)}]^{(a-)}*pH_2O$ where each M=Al.

In a process according to the invention for preparing the inventive metal phosphate, reaction can take place in water and preferably between 20 and 90° C., more preferably between 20 and 60° C. and most preferably between 20 and 40° C.

The present invention further provides a compound obtainable by the above-described process according to the invention.

More particularly, such compounds are notable in that the empirical composition is a melamine aluminum phosphate [(melamine-H)$_2^+$ [AlP$_3$O$_{10}$]$^{2(-)}$]$_z$, has the following $^{31}$P MAS NMR shifts (δ values): −10.6 ppm, −22.0 ppm, −24.5 ppm and −27.6 ppm, and exhibits a single shift around 40 ppm in the $^{27}$Al NMR spectrum. More particularly, the empirical composition is a melamine zinc phosphate [(melamine-H)$_2^+$ [ZnP$_2$O$_7$]$^{2(-)}$]$_z$ with the following $^{31}$P MAS NMR shifts (δ values): +6.2 ppm, +3.7 ppm, +2.0 ppm, −2.5 ppm, −5.5 ppm, −8.2 ppm, −10.7 ppm, −12.1 ppm, −22.2 ppm and −24.7 ppm.

The particular metal phosphate can be prepared, for example, by premixing in the form of powder and/or granules in a mixer and then by homogenizing in a polymer melt by compounding (in a twin-screw extruder among other apparatus). The metal phosphate can possibly also be added directly in the course of processing.

The metal phosphates for the preparation of triazine-intercalated metal phosphates with open framework structures include especially sheet phosphates of the formulae M(H$_2$PO$_4$)$_3$ and M(H$_2$PO$_4$)$_2$ (M=Al, La, Zn or Mn) or M(HPO$_4$)$_2$*nH$_2$O or
M(H$_2$PO$_4$)(PO$_4$).nH$_2$O (M=Ti, Zr, Sn and Ce) and condensed phosphates such as triphosphates or pyrophosphates of the formulae H$_2$AlP$_3$O$_{10}$ and H$_2$ZnP$_2$O$_7$.

However, the systems are best prepared via a reaction with melamine as a template in aqueous acidic metal salt solution. An alternative process consists in the reaction of triazine phosphates with aqueous metal salt solutions (based on Angew. Chem., 1999, 111, 3688-3692).

The metal phosphates with open framework structures thus prepared have orthophosphate (H$_x$PO$_4$ type where x=2, 1 or 0), pyrophosphate or triphosphate as complex ligands, with intercalation of melamine in protonated form (melamine cation) between the lattice layers or into the cavities and widening of the layer spacings in the case of layer structures.

In further processing, the inventive triazine-intercalated metal phosphates are incorporated into a suitable polymer matrix. Suitable polymers which can be used as a substrate are known per se. For incorporation, preference is given to thermoplastic polymers and thermoset polymer systems, rubbers and textiles.

Melamine is preferred as an intercalate.

With orthophosphate as ligands, the novel intercalates can be represented by way of example as follows, where (A-H)$^{(+)}$ (mel-H)$_{(+)}$ (melamine cation):

1. (Mel-H)$_2^{(+)}$[Mn$_3^{2(+)}$(PO$_4$)$_2^{3(-)}$(PO$_3$)$_2^{(-)}$(H$_2$O)$_2$]$^{2(-)}$
2. (Mel-H)$^{(+)}$[Zr$^{4(+)}$(HPO$_4$)$^{2(-)}$(PO$_4$)$^{3(-)}$]$^{(-)}$
3. (Mel-H)$^{(+)}$[Zn$^{2(+)}$(PO$_4$)$^{3(-)}$(H$_2$O)$_4$]$^{(-)}$
4. (Mel-H)$_2^{(+)}$[Zn$^{2(+)}$(H$_2$PO$_4$)$_2^{(-)}$(HPO$_4$)$_2^{2(-)}$]$^{2(-)}$
5. (Mel-H)$^{(+)}$[Zn$_2^{2(+)}$(H$_2$PO$_4$)$_2^{(-)}$(PO$_4$)$^{3(-)}$]$^{2(-)}$
6. (Mel-H)$_2^{(+)}$[Zn$_2^{2(+)}$(H$_2$PO$_4$)$_2^{(-)}$(HPO$_4$)$_2^{2(-)}$]$^{2(-)}$
7. (Mel-H)$_2^{(+)}$[Zn$_2^{2(+)}$(HPO$_4$)$_2^{(-)}$(PO$_4$)$_4^{3(-)}$]$^{2(-)}$
8. (Mel-H)$_4^{(+)}$[Zn$_6^{2(+)}$(HPO$_4$)$_2^{2(-)}$(PO$_4$)$_4^{3(-)}$]$^{4(-)}$
9. (Mel-H)$_2^{(+)}$[Zn$_4^{2(+)}$(HPO$_4$)$_2^{2(-)}$(PO$_4$)$_2^{3(-)}$]$^{2(-)}$
10. (Mel-H)$^{(+)}$[Zn$_4^{2(+)}$(PO$_4$)$_3^{3(-)}$]$^{2(-)}$
11. (Mel-H)$_2^{(+)}$[Zn$_2^{2(+)}$(HPO$_4$)$_3^{2(-)}$]$^{2(-)}$
12. (Mel-H)$^{(+)}$[Zn$_2^{2(+)}$(HPO$_4$)$_2^{(-)}$(PO$_4$)$^{3(-)}$]$^{(-)}$
13. (Mel-H)$^{(+)}$[Zn$^{2(+)}$(H$_2$PO$_4$)$^{(-)}$(HPO$_4$)$^{2(-)}$]$^{(-)}$
14. (Mel-H)$_3^{(+)}$[Al$^{3(+)}$(PO$_4$)$_2^{3(-)}$]$^{3(-)}$
15. (Mel-H)$_2^{(+)}$[Al$_5^{3(+)}$(HPO$_4$)$^{2(-)}$(PO$_4$)$_5^{3(-)}$]$^{2(-)}$
16. (Mel-H)$_2^{(+)}$[Al$_4^{3(+)}$(HPO$_4$)$^{2(-)}$(PO$_4$)$_4^{3(-)}$]$^{2(-)}$
17. (Mel-H)$^{(+)}$[Al$^{3(+)}$(HPO$_4$)$_2^{(-)}$]$^{(-)}$
18. (Mel-H)$^{(+)}$[Al$^{3(+)}$(HPO$_4$)$_2^{2(-)}$H$_2$O]$^{(-)}$
19. (Mel-H)$^{(+)}$[Al$_2^{3(+)}$Co$^{2(+)}$(PO$_4$)$_3^{3(-)}$]$^{(-)}$
20. (Mel-H)$^{(+)}$[Co$^{2(+)}$(PO$_4$)$^{3(-)}$]$^{(-)}$
21. (Mel-H)$^{(+)}$[Sn$^{2(+)}$(PO$_4$)$^{3(-)}$]$^{(-)}$
22. (Mel-H)$_2^{(+)}$[Zr$_2^{4(+)}$(PO$_4$)$_3^{3(-)}$(PO$_3$)]$^{2(-)}$ (mixed type composed of ortho- and pyrophosphate)
23. (Mel-H)$_4^{(+)}$[Zn$_2^{2(+)}$(PO$_4$)$^{3(-)}$(PO$_3$)$_5^{(-)}$]$^{4(-)}$ (mixed type composed of meta- and pyrophosphate)
24. (Mel-H)$^{(+)}$[Zn$_2^{2(+)}$(PO$_4$)$^{3(-)}$(PO$_3$)$_2^{(-)}$]$^{(-)}$ (mixed type composed of meta- and pyrophosphate)
25. (Mel-H)$_2^{(+)}$[Zn$_2^{2(+)}$(PO$_4$)$^{3(-)}$(PO$_3$)$_3^{(-)}$]$^{2(-)}$ (mixed type composed of meta- and pyrophosphate)
26. (Mel-H)$_4^{(+)}$[Zn$_{12}^{2(+)}$(PO$_4$)$_9^{3(-)}$(PO$_3$)$^{(-)}$]$^{4(-)}$ (mixed type composed of ortho- and pyrophosphate)
27. (Mel-H)$_4^{(+)}$[Zn$_6^{2(+)}$(PO$_4$)$_5^{3(-)}$(PO$_3$)$^{(-)}$]$^{4(-)}$ (mixed type composed of ortho- and pyrophosphate)
28. (Mel-H)$_2^{(+)}$[Zn$_4^{2(+)}$(PO$_4$)$_3^{3(-)}$(PO$_3$)$^{(-)}$]$^{2(-)}$ (mixed type composed of ortho- and pyrophosphate)
29. (Mel-H)$_4^{(+)}$[Zn$_4^{2(+)}$(PO$_4$)$_3^{3(-)}$(PO$_3$)$_3^{(-)}$]$^{4(-)}$ (pyrophosphate type)
30. (Mel-H)$_2^{(+)}$[Zn$_4^{2(+)}$(PO$_4$)$_3^{3(-)}$(PO$_3$)$^{(-)}$]$^{2(-)}$ (mixed type composed of ortho- and pyrophosphate)
31. (Mel-H)$_2^{(+)}$[Zn$_2^{2(+)}$(PO$_4$)$^{3(-)}$(PO$_3$)$_3^{(-)}$]$^{2(-)}$ (mixed type composed of meta- and pyrophosphate)
32. (Mel-H)$_4^{(+)}$[Al$_{10}^{3(+)}$(PO$_4$)$_{11}^{3(-)}$(PO$_3$)$^{(-)}$]$^{4(-)}$ (mixed type composed of ortho- and pyrophosphate)
33. (Mel-H)$_4^{(+)}$[Al$_8^{3(+)}$(PO$_4$)$_9^{3(-)}$(PO$_3$)$^{(-)}$]$^{4(-)}$ (mixed type composed of ortho- and pyrophosphate)
34. (Mel-H)$^{(+)}$[Al$^{3(+)}$(PO$_4$)$^{3(-)}$(PO$_3$)$^{(-)}$]$^{(-)}$ (pyrophosphate type)
35. (Mel-H)$_2^{(+)}$[Al$^{3(+)}$(H$_2$PO$_4$)$^{(-)}$(HPO$_4$)$_2^{2(-)}$]$^{2(-)}$
36. (Mel-H)$_2^{(+)}$[Zn$^{2(+)}$(PO$_4$)$^{3(-)}$(PO$_3$)$^{(-)}$]$^{2(-)}$ (pyrophosphate type)
37. (Mel-H)$_2^{(+)}$[Al$^{3(+)}$(PO$_4$)$^{3(-)}$(PO$_3$)$_2^{(-)}$]$^{2(-)}$ (triphosphate type)

it being possible to remove aquo (complexed) water by thermal treatment.

Particular preference is given to 35, 36, 37. Very particular preference is given to 36, 37.

The present invention further provides a process for preparing a flame-retardant deformable polymer, wherein the at least one inventive triazine-intercalated metal phosphate is exfoliated in the polymer.

The invention further provides for the achievement of an anticorrosive protective effect by coating of metal surfaces.

Figure 1:
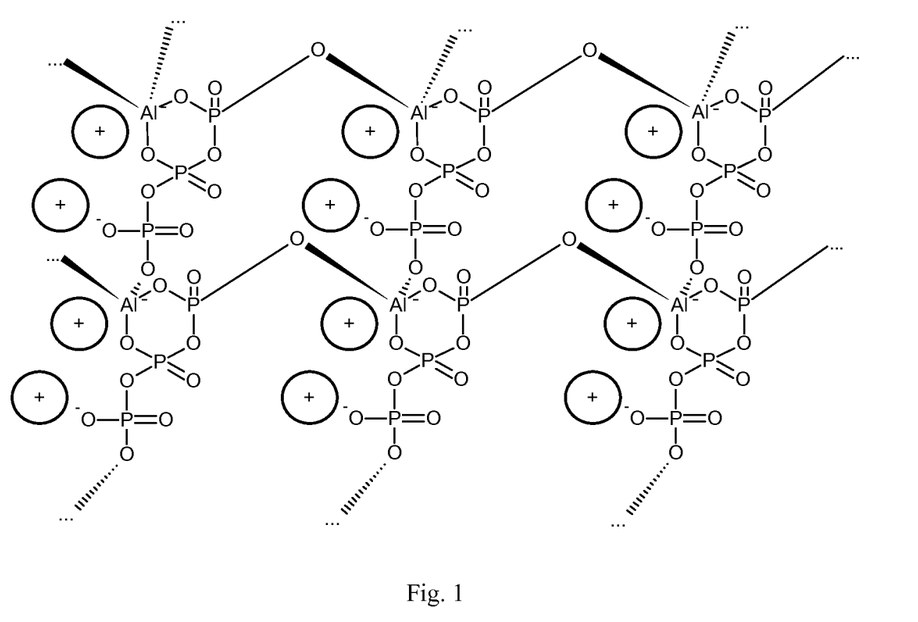
FIG. 1 depicts an example of a lattice section from an intercalation model of one embodiment of a compound.

FIG. 1 shows, by way of example, a lattice section from an intercalation model of melamine in aluminum triphosphate (AlH$_2$P$_3$O$_{10}$) layers (☉=melaminium cation).

The invention is illustrated in detail by examples which follow.

Substances used: melamine (DSM); aluminum tris(dihydrogenphosphate) (50% solution in water) (PRAYON Deutschland), zinc oxide, ortho-phosphoric acid (ALDRICH)

EXAMPLE 1: SYNTHESIS OF BISMELAMINE ALUMINODIHYDROGENPHOSPHATE BIS(HYDROGENPHOSPHATE)

(Product A)—Precursor Compound (a=2, M=Al, b=1, m=3, $x_1$=1, $x_2$=2, $x_3$=0, y=0, p=0)

100.9 g (0.8 mol) of melamine are dissolved in 2.4 l of water while stirring and heating (40 to 60° C.). In this solution, 254.4 g (0.4 mol) of aluminum tris(dihydrogenphosphate) (50% solution in water) are added dropwise, which forms a thick slurry. This is followed by stirring for 30 min, cooling to room temperature, removal of the white precipitate formed by filtration with suction, washing with water and drying to constant weight at 120° C.

Yield: 211.7 g, corresponds to 92.8% of theory.

Elemental analysis: C: 12.7% (12.6%); H: 3.3% (3.2%); N: 29.9% (29.5%); Al: 4.7% (4.7%); P: 16.4% (16.3%) (theoretical values)

EXAMPLE 2: SYNTHESIS OF BISMELAMINE ALUMINOTRIPHOSPHATE (Product B)

(a=2, M=Al, b=1, m=3, $x_1$=0, $x_2$=0, $x_3$=1, y=2, p=0)

Product (A) is heated to a virtually constant weight at 280° C. with frequent mixing for 5 h. The resulting white product has the following composition:

Elemental analysis: C: 13.5% (13.5%); H: 2.6% (2.6%); N: 30.1% (31.5); Al: 5.1% (5.1%); P: 17.5% (17.4%) (theoretical values)

Figure 2:
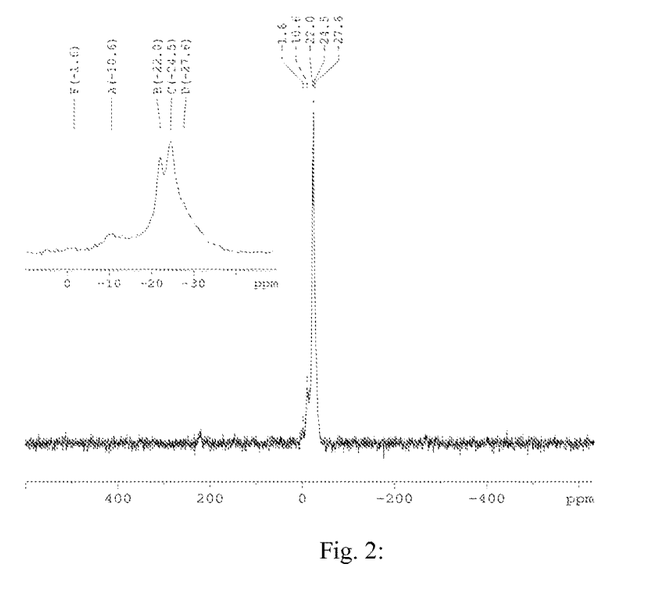
FIG. 2 depicts the quantitative $^{31}$P NMR spectrum of the bismelamine aluminotriphosphate of Example 2.

$^{31}$P MAS NMR shifts (δ values): −10.6 ppm, −22.0 ppm, −24.5 ppm and −27.6 ppm (see FIG. 2). FIG. 2 here shows the quantitative $^{31}$P NMR spectrum of bismelamine aluminotriphosphate (product B) ($v_{MAS}$=20 KHz, $^1$H-decoupled)).

Figure 4:
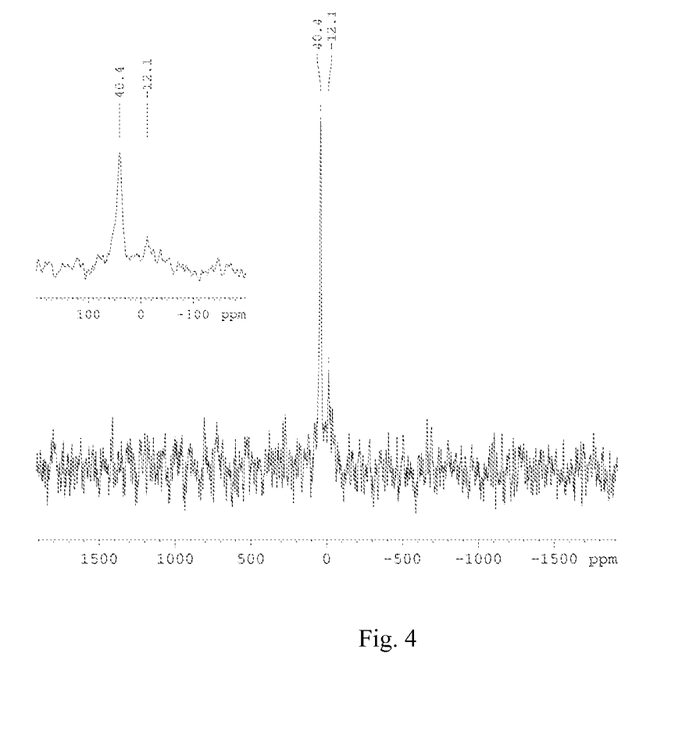
FIG. 4 depicts the $^{27}$Al NMR spectrum of the bismelamine alumintriphosphate of Example 2.

$^{27}$Al NMR spectrum: sole shift around 40 ppm (see FIG. 4, $v_{MAS}$=20 KHz).

COMPARATIVE EXAMPLE 3: SYNTHESIS OF TRISMELAMINE ALUMINOTRIS(HYDROGENPHOSPHATE) DIHYDRATE (Product C)—Precursor Compound (a=3, M=Al, b=1, m=3, $x_1$=0, $x_2$=3, $x_3$=0, y=0, p=2).

94.6 g (0.75 mol) of melamine are dissolved in 2.3 l of water while stirring and heating. To this solution are added dropwise 159.0 g (0.25 mol) of aluminum tris(dihydrogenphosphate) (50% solution in water), which forms a voluminous slurry. This is followed by stirring for 30 minutes, cooling to room temperature, removal of the white precipitate formed by filtration with suction, washing twice with water and drying to constant weight at 120° C. Yield: 174.0 g, corresponds to 95.0% of theory.

Elemental analysis: C: 14.8% (14.8%); H: 3.5% (3.9%); N: 33.8% (34.4%) (theoretical values)

EXAMPLE 4: SYNTHESIS OF PRODUCT B PROCEEDING FROM PRODUCT C

Preparation of Product C as in Example 3, but with subsequent heat treatment at 210° C. for 5 h. This results in trismelamine aluminotris(dihydrogenphosphate) monohydrate as a precursor.

$(C_3H_7N_6)_3^{(+)}[Al(HPO_4)_3]^{3(-)} \cdot H_2O$.

Yield: 165.7 g, corresponds to 92.8% of theory.
Elemental analysis: C: 15.1% (15.1%); H: 4.3% (3.7%); N: 35.1% (35.3%); (theoretical values)
Product B is obtained from this precursor by renewed heat treatment at 280° C., 6 h, and a decrease in weight of 25% takes place. The result is bismelamine aluminotriphosphate $(C_3H_7N_6)_2^{(+)}[Al^{3(+)}(APO_4)^{3(-)}(PO_3)_2^{(-)}]^{2(-)}$ (quant. yield)
Elemental analysis: C: 13.4% (13.5%); H: 4.0% (2.6%); N: 29.7% (31.5%); (theoretical values)

It is evident from this that an alternative route to Product B is possible by use of Product C. However, this process is uneconomic in practice since about one third of the melamine used has to be removed again by heat treatment.

If, however, the heat treatment is dispensed with, incorporation into polyamides, polycarbonates and polyesters is greatly complicated since significant amounts of melamine sublime off. In the case of use of Product B prepared according to Example 2, these difficulties, however, do not occur.

EXAMPLE 5: SYNTHESIS OF BISMELAMINE ZINCODIPHOSPHATE (Product D)

Figure 3:
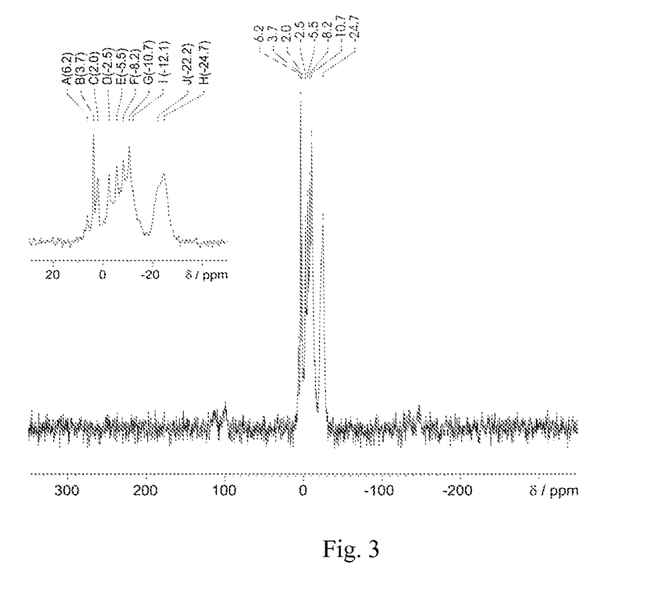
FIG. 3 depicts the $^{31}$P NMR spectrum of the bismelamine zincodiphosphate of Example 5.

$(C_3H_7N_6)_2^{(+)}[Zn^{2(+)}(PO_4)^{3(-)}PO_3)^{(-)}]^{2(-)}$ (a=2, M=Zn, b=1, m=2, $x_1$=0, $x_2$=0, $x_3$=1, y=1, p=0).
Product D obtained by the above method is dried at 280° C. for 5 h, and a decrease in weight of approx. 6.0% takes place.
Elemental analysis: C: 15.1% (14.6%); H: 2.8% (2.9%); N: 34.0% (34.1%); Zn: 12.6% (13.3%); P: 12.2% (12.2%). (theoretical values)
$^{31}$P MAS NMR shifts (δ values): +6.2 ppm, +3.7 ppm, +2.0 ppm, −2.5 ppm, −5.5 ppm, −8.2 ppm, −10.7 ppm, −12.1 ppm, −22.2 ppm and −24.7 ppm. (see FIG. 3). FIG. 3 here shows the quantitative $^{31}$P NMR spectrum of bismelamine zincodiphosphate (Product D) ($v_{MAS}$=20 KHz).

EXAMPLE 6: STATIC THERMAL TREATMENT OF PRECURSOR PRODUCTS A AND C

The results are summarized in Tab. 1.

TABLE 1

| Thermal treatment of precursor products | | |
|---|---|---|
| | Product A (%) | Product C (%) |
| | 100 | 100 |
| 200° C./2 h | 94.9 | 93.9 |
| 240° C./2 h | 91.4 | 86.0 |
| 280° C./2 h | 89.5 | 82.4 |
| 300° C./2 h | 85.9 | 77.7 |
| 300° C./4 h | 82.7 | 76.0 |

As is clear from Table 1, the inventive Product A is much more thermally stable than the prior art Product C (WO-A 2009/015772). This behavior was surprising since it was unforeseeable.

EXAMPLE 7: STATIC THERMAL TREATMENT OF THE HEAT TREATMENT PRODUCTS B, D AND MPP (MELAMINE POLYPHOSPHATE, PRIOR ART)

The results are summarized in Tab. 2.

TABLE 2

| Thermal treatment of heat treatment products | | | |
|---|---|---|---|
| | Product B (%) | Product D (%) | Product MPP (%) |
| | 100 | 100 | 100 |
| 200° C./2 h | 99.8 | 99.2 | 99.1 |
| 240° C./2 h | 99.5 | 98.9 | 98.9 |
| 280° C./2 h | 98.3 | 97.4 | 98.0 |
| 300° C./2 h | 94.3 | 94.1 | 91.3 |
| 300° C./4 h | 89.7 | 92.7 | 83.7 |

As is evident from Table 2, the inventive Products B and D are much more thermally stable than the prior art MPP. This behavior was surprising since it was unforeseeable.

Performance Testing in PVC

I. Production of the Milled Sheet:

The dry mixtures prepared according to Table 1 (R-1, R-2) are each plasticized in a Collin analytical laboratory roll mill (Model: W100E, manufactured: 2005, from COLLIN) at the temperature specified (roll diameter: 110 mm, 15 rpm, friction: −15%) for 5 minutes. The films thus obtained (thickness 0.3 mm) are sent to further tests.

II. Conduction of the Static Heat Test (SHT):

Test strips (15 mm×15 mm) are cut out of the milled sheets according to I. These are stressed in a METRASTAT IR 700 test oven (DR. STAPFER GmbH, Dusseldorf) at the temperature specified until significant discoloration. Thereafter, the YI (yellowness index) is determined to DIN 53381 with a Spectro-Guide colorimeter (from BYK-GARDNER) and compared with the YI of the unstressed milled sheet (zero minute value). The results are summarized in tabular form. The smaller the YI at a particular time, the better the color characteristics.

III. Conduction of Flame Retardancy Testing:

The milled sheets produced above are processed to give pressed slabs (120×100×3 mm) and subjected to a flame retardancy test based on UL94. The UL94 test is described in *"Flammability of Plastic Materials for Parts in Devices and Appliances"*, 5th edition, October, 1996.

IV. Determination of the Mechanical Properties:

The mechanical properties were determined by means of Instron 5569 (5 kN side action grips) to ASTM D412.

V. Conduction of the NMR Measurements:

All measurements were conducted on a Bruker Avance II 200 solid state MAS spectrometer with a 4.7 T magnet and a double resonance sample head for 2.5 mm rotors under magic angle spinning conditions (MAS). The rotation frequencies $v_{MAS}$ used are specified for the corresponding measurements. Chemical shifts are reported relative to the reference substances currently recommended by IUPAC ($^{27}$Al: 1.1 M Al(NO$_3$)$_3$ in D$_2$O; $^{31}$P: 85% phosphoric acid), and the spectrometer calibration was undertaken with the aid of the standardized shift scale from the proton resonance of TMS.

The following formulations were tested:

EXAMPLE 8: TESTING IN FLEXIBLE PVC

The following dry mixtures are prepared (Table 3)—Starting weights in parts by weight:

TABLE 3

| | Formulations | |
|---|---|---|
| Components | (R-1) | (R-2) |
| PVC (Evipol SH 7020) K value = 70 | 100 | 100 |
| Plasticizer (DINP)[1] | 50 | 50 |
| Zinc stearate | 0.6 | 0.6 |
| Hydrotalcite[2] | 2.9 | 2.9 |
| Antioxidant (bisphenol A) | 0.5 | 0.5 |
| Flame retardant 1 (ATH)[3] | 60 | 25 |
| Flame retardant 2 (Product B) | — | 5 |
| Flame retardancy effect (burn time in sec. after 3 ignitions) | 0/1/1 | 0/1/1 |

[1] diisononyl phthalate, ex BASF
[2] Sorbacid 911, ex SÜD CHEMIE
[3] aluminum trihydroxide, APYRAL 40CD, ex NABALTEC As evident from Table 3, the performance of the inventive formulation (R-2) is comparable to the prior art example (R-1).

TABLE 4

| | SHT (200° C.) according to II | |
|---|---|---|
| Time [min] | (R-1) | (R-2) |
| 3 | 10.3 | 5.8 |
| 6 | 10.0 | 5.5 |
| 9 | 11.0 | 5.7 |
| 12 | 11.5 | 6.4 |
| 15 | 12.9 | 7.4 |
| 18 | 13.9 | 8.6 |
| 21 | 15.5 | 10.3 |
| 24 | 18.8 | 12.7 |
| 27 | 22.0 | 15.8 |
| 30 | 25.8 | 19.3 |
| 33 | 31.7 | 24.9 |
| 36 | 40.3 | 33.3 |
| 39 | 52.9 | 44.5 |
| 42 | 70.5 | 62.7 |
| 45 | 95.3 | 76.7 |
| 48 | 110.8 | 85.5 |
| 51 | 117.2 | 89.2 |
| 54 | 118.4 | 90.9 |
| 57 | 117.6 | 91.3 |
| 60 | 115.72 | 92.4 |

As evident from Table 4, the inventive formulation (R-2) has significantly better color characteristics, especially in relation to the initial color, than the noninventive formulation (R-1).

TABLE 5

| | Mechanical properties | | |
|---|---|---|---|
| | Tensile strength [MPa] | Breaking strain [%] | Young's modulus [MPa] |
| (R-1) | 13.64 | 331.38 | 33.59 |
| (R-2) | 15.24 | 368.45 | 25.27 |

Table 5 shows that the mechanical properties of the inventive formulation (R-2) are actually improved compared to the prior art (R-1).

The invention claimed is:
1. A flame retardant composition comprising:
(a) at least one triazine-intercalated metal phosphate with at least one monomer unit of the following general formula (I):

$(A-H)_a^{(+)}[M_b^{m+}(H_2PO_4)_{x1}^{(-)}(HPO_4)_{x2}^{2(-)}(PO_4)_{x3}^{3(-)}(PO_3)_y^{(-)}]^{(a-)*}pH_2O$ (I)

where $(A-H)^{(+)}$ is a triazine derivative of the formula (II-1), (II-2) or (II-3)

melamine (II-1)

melam (II-2)

melem (II-3)

each M is independently Cu, Mg, Ca, Zn, Mn, Fe, Co, Ni, TiO, ZrO, VO, B, Si, Al, Sb, La, Ti, Zr, Ce, or Sn;
a is 1 to 6,
b is 1 to 14,
m=1 to 4,
$x_1$, $x_2$, $x_3$, y=0 to 12, where at least one of the variables $x_1$, $x_2$, $x_3 > 0$ and p=0 to 5,
where: $a+mb=x_1+2x_2+3x_3+y$,
where the at least one monomer excludes the compounds of formulas $[(A-H)^+]_c[M^{c+}(HPO_4^{2-})_c]$, and (III-1)

$[(A-H)^+]_c[M^{c+}(P_2O_7^{4-})_{c/2}]$, (III-2)

wherein M is Ca, Mg, Zn, or Al, and c is the oxidation number of the metal, and (b) at least one further flame retardant component other than (a).

2. The composition according to claim 1, characterized in that the at least one further component (b) is a metal compound which is not a metal phosphate of component (a), or/and at least one metal-free phosphorus compound.

3. The composition according to claim 1, characterized in that $(A-H)^{(+)}=(II-1)$ and M=Zn or Al.

4. The composition according to claim 2, characterized in that the at least one metal compound (b) is a metal oxide, a metal hydroxide, a metal phosphate, a metal pyrophosphate, a hydrotalcite, a cationically or anionically modified organoclay, a stannate or molybdate salt, a metal borate or metal phosphinate of the formula (III):

(III)

where $R^1$ and $R^2$ are each hydrogen or a straight-chain or branched $C_1$-$C_6$-alkyl radical or a phenyl radical; and Mt=Ca, Mg, Zn, or Al, and m=2 or 3.

5. The composition according to claim 2, characterized in that the at least one metal compound (b) is diantimony trioxide, diantimony tetroxide, diantimony pentoxide, or zinc oxide.

6. The composition according to claim 2, characterized in that the at least one metal compound (b) is magnesium hydroxide (brucite), aluminum trihydroxide (ATH, gibbsite), or aluminum monohydroxide (boehmite).

7. The composition according to claim 2, characterized in that the at least one metal compound (b) is magnesium aluminum hydroxo carbonate or calcium aluminum hydroxo carbonate.

8. The composition according to claim 2, characterized in that the at least one metal compound (b) is an alkyl sulfate- or fatty acid carboxylate-modified hydrotalcite or a long-chain quaternary ammonium-modified clay mineral.

9. The composition according to claim 2, characterized in that the at least one metal compound (b) is ammonium heptamolybdate, ammonium octamolybdate, zinc stannate, or zinc hydroxystannate.

10. The composition according to claim 2, characterized in that the at least one metal compound (b) is an alkali metal borate, alkaline earth metal borate, or zinc borate.

11. The composition according to claim 2, characterized in that the at least one metal compound (b) is calcium phosphinate, magnesium phosphinate, zinc phosphinate or aluminum phosphinate (hypophosphite), calcium phenyl (benzene)phosphinate, magnesium phenyl(benzene)phosphinate, zinc phenyl(benzene)phosphinate or aluminum phenyl(benzene)phosphinate, or calcium diethyl(ethane) phosphinate, magnesium diethyl(ethane)phosphinate, zinc diethyl(ethane)phosphinate or aluminum diethyl(ethane) phosphinate.

12. The composition according to claim 2, characterized in that the at least one metal-free phosphorus compound (b) is red phosphorus, an oligomeric phosphate ester, an oligomeric phosphonate ester, a cyclic phosphonate ester, a thiopyrophosphoric ester, a melamine polyphosphate or ammonium polyphosphate, a hydroxyalkylphosphine oxide, a tetrakis(hydroxyalkyl)phosphonium salt, a phospholane (oxide) derivative or dihydrophosphole (oxide) derivative, or a phosphonite ester.

13. The composition according to claim 2, characterized in that the at least one metal-free phosphorus compound is an oligomeric phosphate ester of the formula (IV) or formula (V):

(IV)

(V)

where each R is independently hydrogen, $C_1$-$C_4$ alkyl or hydroxyl, n=1 to 3 and o is 1 to 10.

14. The composition according to claim 2, characterized in that the at least one metal-free phosphorus compound is an oligomeric phosphonate ester of the formula (VI):

(VI)

where $R^3$=methyl or phenyl and x is 1 to 20, and where each R is independently hydrogen, $C_1$-$C_4$ alkyl or hydroxyl, and n=1 to 3.

15. The composition according to claim 2, characterized in that the at least one metal-free phosphorus compound is a cyclic phosphonate ester of the formula (VII):

(VII)

where y=0 or 2.

16. The composition according to claim 2, characterized in that the at least one metal-free phosphorus compound is a thiopyrophosphoric ester of the formula (VIII):

(VIII)

17. The composition according to claim 2, characterized in that the at least one metal-free phosphorus compound is present as a phosphonite ester in the form of a benzenemonophenyl ester derivative or as a DOPO derivative (9,10-dihydro-9-oxa-10-phosphaphenanthrene 10-oxide or 6H-dibenzo(c,e)(1,2)oxaphosphorin-6-one derivative) of the formula (IX) or (X):

(IX)

(X)

18. The composition according to claim 2, characterized in that polyols and/or aminouracils and/or polyhedral oligomeric silsesquioxane compounds and/or trishydroxyethyl isocyanurate and/or melamine cyanurate and/or expandable graphite are additionally present.

19. The composition according to claim 18, characterized in that the polyol is pentaerythritol, dipentaerythritol, or tripentaerythritol, the aminouracil is 1,3-dimethyl-6-aminouracil, and the polyhedral oligomeric silsesquioxane compound is methoxysilane-based.

20. The composition according to claim 1, characterized in that the concentration of the at least one triazine-intercalated metal phosphate (a) and of component (b) in a polymer or a polymer mixture is preferably 0.1 to 60% by weight based on the polymer to be processed.

21. A method of using a composition according to claim 1 as a flame retardant in a polymer, paper, textile, or wood plastic composite (WPC).

22. The method according to claim 21, characterized in that the polymer is a thermoplastic, or is a thermoset.

* * * * *

UNITED STATES PATENT AND TRADEMARK OFFICE
CERTIFICATE OF CORRECTION

PATENT NO. : 9,708,538 B2
APPLICATION NO. : 13/818672
DATED : July 18, 2017
INVENTOR(S) : Hans-Günter Köstler, Trupe Dave and Wolfgang Wehner Page 1 of 1

It is certified that error appears in the above-identified patent and that said Letters Patent is hereby corrected as shown below:

In the Specification

At Column 22, Lines 35-50, delete:

And insert:

Signed and Sealed this
Ninth Day of January, 2018

Joseph Matal
*Performing the Functions and Duties of the
Under Secretary of Commerce for Intellectual Property and
Director of the United States Patent and Trademark Office*